United States Patent
Chang

(10) Patent No.: US 7,115,283 B2
(45) Date of Patent: Oct. 3, 2006

(54) PREPARATIONS FOR SUSTAINED RELEASE OF NUTRACEUTICALS AND METHODS OF CONTROLLABLY RELEASING NUTRACEUTICALS

(75) Inventor: David S. Chang, Fullerton, CA (US)

(73) Assignee: Access Business Group International LLC, Ada, MI (US)

( * ) Notice: Subject to any disclaimer, the term of this patent is extended or adjusted under 35 U.S.C. 154(b) by 251 days.

(21) Appl. No.: 10/430,680

(22) Filed: May 6, 2003

(65) Prior Publication Data
US 2004/0221868 A1 Nov. 11, 2004

(51) Int. Cl.
*A01N 65/00* (2006.01)
(52) U.S. Cl. ...................................... 424/725
(58) Field of Classification Search ................ 424/725
See application file for complete search history.

(56) References Cited

U.S. PATENT DOCUMENTS

| | | | |
|---|---|---|---|
| 2,816,061 A | 12/1957 | Doerr et al. | |
| 2,887,440 A | 5/1959 | Greminger, Jr. et al. | |
| 2,940,901 A | 6/1960 | Hiatt et al. | |
| 3,437,728 A | 4/1969 | Renwanz et al. | |
| 4,385,078 A | 5/1983 | Onda et al. | |
| 4,415,547 A | 11/1983 | Yu et al. | |
| 4,851,233 A | 7/1989 | Khan et al. | |
| 5,008,113 A | 4/1991 | Kokubo et al. | |
| 5,068,112 A | 11/1991 | Samejima et al. | |
| 5,376,384 A | 12/1994 | Eichel et al. | |
| 5,478,573 A | 12/1995 | Eichel et al. | |
| 5,529,790 A | 6/1996 | Eichel et al. | |
| 5,622,721 A * | 4/1997 | Dansereau et al. | 424/490 |
| 5,681,582 A | 10/1997 | Gilis et al. | |
| 5,830,503 A | 11/1998 | Chen | |
| 5,895,663 A | 4/1999 | Irwin et al. | |
| 5,989,557 A | 11/1999 | Bombardelli et al. | |
| 6,129,933 A | 10/2000 | Oshlack et al. | |
| 6,168,806 B1 | 1/2001 | Lee et al. | |
| 6,299,925 B1 * | 10/2001 | Xiong et al. | 426/597 |
| 6,316,031 B1 | 11/2001 | Oshlack et al. | |
| 6,410,052 B1 * | 6/2002 | Morre et al. | 424/468 |
| 6,410,061 B1 | 6/2002 | Morré et al. | |
| 6,428,818 B1 | 8/2002 | Morré et al. | |
| 2003/0170319 A1 * | 9/2003 | Netke et al. | 424/682 |
| 2004/0132821 A1 * | 7/2004 | Crea | 514/563 |
| 2004/0180866 A1 * | 9/2004 | Mamchur | 514/170 |

OTHER PUBLICATIONS

PubMed Abstract No. 12575156: Li, Y.; Huang, C.; Cen, Y.; Xu, S.; and Xu, S. "Preparation of Tea Polyphenols Sustained-Release Microcapsule"; Zhong Yao Cai, 2000, 23(5), 281-4.

* cited by examiner

*Primary Examiner*—Michael Meller
(74) *Attorney, Agent, or Firm*—Brinks Hofer Gilson & Lione; Gregory H. Zayia

(57) ABSTRACT

Preparations for the sustained release of a nutraceutical are described that include a solid matrix coated with a methyl-cellulose-containing coating. The solid matrix contains a polyphenol and the nutraceutical. Methods of controllably releasing a nutraceutical are also described that include administering to a patient a preparation containing a solid matrix coated with methylcellulose-containing coating. The solid matrix includes a polyphenol and a therapeutically effective amount of the nutraceutical.

15 Claims, 5 Drawing Sheets

PREPARATIONS FOR SUSTAINED RELEASE OF NUTRACEUTICALS AND METHODS OF CONTROLLABLY RELEASING NUTRACEUTICALS

BACKGROUND

The present invention relates to preparations and methods for the controlled release of nutraceuticals.

The controlled release of a physiologically active agent into an individual's system from a sustained release dosage form is often a desirable alternative to repeated administrations (e.g., after a prescribed number of hours) of the agent from conventional dosage forms (i.e., one controlled release dosage may provide the full daily regimen of active agent). Sustained release formulations incorporating water soluble cellulose ethers in a hydrophilic solid core matrix have been developed for this purpose. Upon contact with an aqueous environment, such formulations hydrate to form a gel layer on the surface of the solid core matrix, which limits entry of water into the solid core, thereby establishing a diffusion-controlled sustained release of the active ingredient therein.

Alternative sustained release formulations are based on solid core matrixes that have been coated with materials that can form membranes exhibiting sustained release characteristics. Examples of such materials include hydroxypropyl methylcellulose, shellac, fats, and waxes.

In view of the importance of controlled release delivery systems for the administration of physiologically active agents, there persists a need for new preparations capable of slowly releasing an ingredient from a solid matrix in which it is contained.

SUMMARY

The scope of the present invention is defined solely by the appended claims, and is not affected to any degree by the statements within this summary. By way of introduction, a first preparation for the sustained release of a nutraceutical embodying features of the present invention includes a solid matrix coated with a coating comprising methylcellulose. The solid matrix contains a polyphenol and a therapeutically effective amount of the nutraceutical.

A second preparation for the sustained release of a nutraceutical embodying features of the present invention includes a solid matrix coated with a coating comprising methylcellulose. The solid matrix contains a polyphenol and the nutraceutical.

A third preparation for sustained release of a nutraceutical embodying features of the present invention includes a solid matrix coated with a coating containing at least about 90 percent by weight of methylcellulose. The solid matrix contains a polyphenol derived from green tea extract and a therapeutically effective amount of the nutraceutical. The polyphenol constitutes from about 5 to about 20 percent by weight of the solid matrix.

A method of controllably releasing a nutraceutical embodying features of the present invention includes administering to a patient a preparation containing a solid matrix coated with a coating containing methylcellulose. The solid matrix includes a polyphenol and a therapeutically effective amount of the nutraceutical.

DETAILED DESCRIPTION

Figure 1:
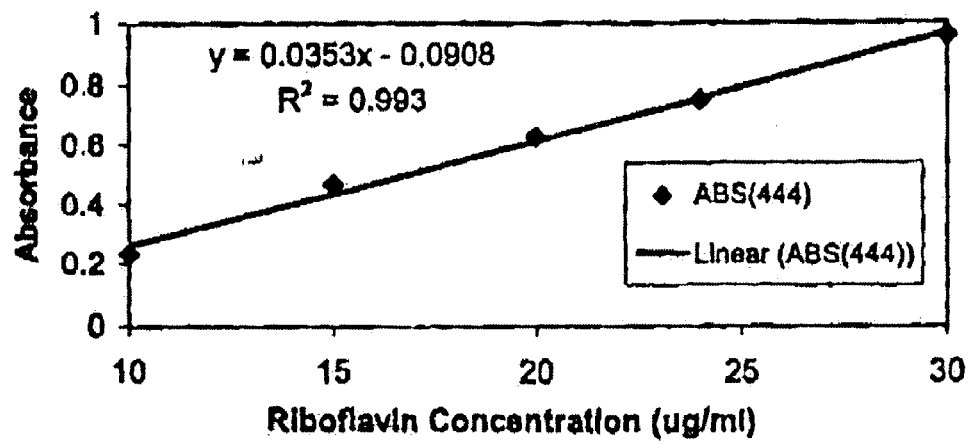
FIG. 1 shows a riboflavin calibration curve.

It has been discovered that when a solid matrix containing a polyphenol is coated with a coating containing methylcellulose, a preparation exhibiting good levels of sustained release activity may be provided. Without wishing to be bound by a particular theory or to in any way limit the scope of the appended claims and their equivalents, it is presently believed that the interaction of the methylcellulose in the coating with the polyphenol compound in the solid matrix results in formation of a poorly soluble film that provides sustained release activity. Moreover, it has been discovered, surprisingly and unexpectedly, that the sustained release activity observed for a solid matrix coated with a coating containing methylcellulose is significantly better than that observed for a solid matrix coated with 100% hydroxypropyl methylcellulose. Preparations and methods embodying features of the present invention are described hereinbelow.

Throughout this description and in the appended claims, the following definitions are to be understood:

The term "nutraceutical" refers to any agent or combination of agents that produces a physiological effect in a mammal.

The phrase "therapeutically effective amount" refers to an amount of nutraceutical that, when used in accordance with methods embodying features of the present invention, enables a target effect to be achieved in a particular subject.

The phrase "solid matrix" refers to a solid phase carrier medium.

The term "polyphenol" refers to a compound containing a plurality (i.e., two or more) of hydroxyl groups. Representative polyphenols for use in accordance with the present invention include but are not limited to flavanols (catechins), flavonols, anthocyanins, catechin oligomers (procyanidins), flavonoids, cinnamate derivatives, and the like, and combinations thereof. Polyphenols suitable for use in accordance with the present invention are described in the review article entitled "The Flavonoids. A Class of Semi-Essential Food Components: Their Role in Human Nutrition" by Joachim Kuhnau (*Wld Rev. Nutr. Diet,* 1976, 24, pp. 117–191) and in the review article entitled "Flavonoids as Medicinal Agents—Recent Advances" by D. Pathak, K. Pathak, and A. K. Singla (*Fitoterapia,* 1991, LXII, No. 5, pp. 371–389). The entire contents of both review articles are incorporated herein by reference, except that in the event of any inconsistent disclosure or definition from the present application, the disclosure or definition herein shall be deemed to prevail.

Desirable polyphenols for use in accordance with the present invention are naturally-occurring, such as may be found among the class of phytochemicals. Presently desirable polyphenols include but are not limited to green tea extracts (e.g., catechin, epicatechin, gallocatechin, gallocatechin gallate, epigallocatechin, epicatechin gallate, epigallocatechin gallate, etc.), grape seed extracts (e.g., anthongandiding, oligomeric proanthocyanidins or proanthanols, etc.), and combinations thereof.

The term "phytochemical" refers to any species produced by and/or obtained from a plant.

The phrase "full release" as applied to solid matrices embodying features of the present invention refers to release of at least about 95% of an agent from a solid matrix.

A preparation for sustained release of a nutraceutical that embodies features of the present invention includes a solid matrix coated with a coating containing methylcellulose. The solid matrix contains a polyphenol and the nutraceutical. Desirably, the nutraceutical is present in a therapeutically effective amount.

The polyphenol in the solid matrix may be a separate ingredient distinct from the nutraceutical, such that the solid matrix contains a minimum of 2 ingredients. Alternatively, in the case of multi-agent-containing nutraceuticals that contain at least one polyphenolic ingredient or in the case of single-agent nutraceuticals that are themselves polyphenols, the polyphenol of the solid matrix may be provided by the polyphenolic ingredient and/or portion of the nutraceutical, such that additional polyphenol is not required (although it may be desirable to add additional polyphenol in certain applications).

Desirably, the solid matrix used in accordance with the present invention is selected from the group consisting of tablets, particles, powders (i.e., a composite of individual particles), granules (i.e., an agglomeration of smaller particles that form larger particles), capsules, caplets, and combinations thereof. Without wishing to be bound by a particular theory or to in any way limit the scope of the appended claims and their equivalents, it is presently believed that the intimacy of contact between the polyphenol in the solid matrix and the methylcellulose in the coating affects sustained release activity. Accordingly, it is desirable that the solid matrix not present an undue barrier to interaction between the polyphenol and methylcellulose, which might result with certain types of gelatin capsulation materials. Accordingly, non-encapsulated materials are desirable at present. Moreover, tablets, granules, and particles are presently desirable solid matrices for use in accordance with the present invention.

Desirably, the polyphenol used in accordance with the present invention is naturally occurring. Green tea or one or more individual polyphenols derived from green tea are particularly desirable at present. Throughout this description and in the appended claims, phrases such as "the polyphenol is derived from green tea" are to be understood as referring to the use of green tea in, for example, its unmodified, commercially available form as well as to extracts of green tea that are obtained, for example, via a separation and/or purification process. In addition, the use of green tea is to be considered as descriptive. One of ordinary skill in the art will understand that other sources of polyphenols can be used in accordance with the present invention.

While the amount of polyphenol in the solid matrix is not limited, it is desirable that the polyphenol comprise less than about half of the weight of the solid matrix. When the polyphenol is green tea or an extract derived from green tea, it is desirable that the polyphenol comprises from about 1 to about 50 percent by weight of the solid matrix, more desirably from about 2 to about 40 percent by weight of the solid matrix, more desirably from about 3 to about 30 percent by weight of the solid matrix, more desirably from about 4 to about 25 percent by weight of the solid matrix, and more desirably from about 5 to about 20 percent by weight of the solid matrix.

All manner of physiologically active agents (i.e., nutraceuticals) that can be advantageously administered via controlled delivery are contemplated for use in accordance with the present invention. Representative active agents include but are not limited to antioxidants, antibiotics, antihistamines, antifungals, antimicrobials, analgesics, free radical scavengers, anti-tumor drugs, antiviral agents, HIV inhibitors, anti-inflammatory agents, antihepatoxic agents, anthelmintics, enzyme-inhibitors, vitamins, minerals, and the like, and combinations thereof.

Nutraceuticals suitable for use in accordance with the present invention may be derived from natural sources or prepared synthetically. Phytochemicals obtained from fruits and vegetables (e.g., polyphenols) are especially desirable for use in accordance with the present invention. Suitable representative naturally-occurring nutraceuticals include but are not limited to bioflavonoids, catechin-based preparations such as proanthanol and proanthocyanidin, acerola concentrate, grape seed extract, pycnogenol, provatene, carotenoids such as β-carotene, sodium bisulfite, vitamins such as Vitamin E, riboflavin (Vitamin $B_2$), and Vitamin C (L-ascorbic acid), α-tocopherol, all manner of herbal compounds, elderberry extract, lutein, coenzyme Q10, and the like, and combinations thereof.

The duration of sustained release of a nutraceutical in accordance with the present invention may be modified by varying the thickness of the methylcellulose-containing coating on the solid matrix and/or by varying the amount of methylcellulose contained in the coating. Throughout this description, in order to simplify the discussion, slower, more prolonged release of nutraceutical is generally described as being "better" and/or "more desirable" than faster, more rapid release of nutraceutical. However, it is to be understood that any assessment of "good," "bad" or "better" sustained release activity is related to the particular requirements for administering a specific nutraceutical. Thus, with some nutraceuticals, it may be desirable to release the nutraceutical from the solid matrix more rapidly than with other nutraceuticals. All manner of sustained release durations that may be achieved in accordance with the claimed invention—some slower than others—have been contemplated for use and are included within the scope of the present invention.

Desirably, the nutraceutical in the solid matrix is released over a time span of at least 3 hours, more desirably at least 5 hours, and still more desirably at least 8 hours. As shown by the Examples below, the full release of nutraceutical from a solid matrix that does not contain green tea extract occurs in a time frame that is as short as 2–3 hours. By contrast, surprisingly and unexpectedly, only about 80% of nutraceutical is released after 8 hours when green tea is included in the solid matrix.

With regard to thickness of the methylcellulose-containing coatings embodying features of the present invention, it is presently desirable that the solid matrix be coated with the coating to at least about a 1% weight gain, more desirably to at least about a 2% weight gain, more desirably to at least about a 3% weight gain, more desirably to at least about a 4% weight gain, and still more desirably to at least about a 5% weight gain.

With regard to the amount of methylcellulose contained in the methylcellulose-containing coatings embodying features of the present invention, it is presently desirable that the coating contain at least about 10% by weight of methylcellulose, more desirably at least about 20% by weight of methylcellulose, more desirably at least about 30% by weight of methylcellulose, more desirably at least about 40% by weight of methylcellulose, more desirably at least about 50% by weight of methylcellulose, more desirably at least about 60% by weight of methylcellulose, more desirably at least about 70% by weight of methylcellulose, more desirably at least about 80% by weight of methylcellulose, more desirably at least about 90% by weight of methylcellulose, and still more desirably about 100% by weight of methylcellulose.

Tablet coatings that contain less than 100% by weight of methylcellulose desirably are admixed with one or more additional materials that are themselves capable of providing a degree of sustained release. Such materials include but are not limited to hydroxypropyl methylcellulose, ethylcellulose, cellulose acetate, acrylic esters, shellac, fats, waxes, and the like, and combinations thereof. Coatings containing a mixture of hydroxypropyl methylcellulose and methylcellulose represent a series of binary coating mixtures embodying features of the present invention. For such binary mixtures, all manner of weight ratios of hydroxypropyl methylcellulose to methylcellulose are contemplated, including but not limited to the following: 10/90, 20/80, 30/70, 40/60, 50/50, 60/40, 70/30, 80/20, and 90/10. Mixtures containing at least about 50 percent by weight of methylcellulose are especially desirable.

All manner of peroral dosage forms suitable for peroral administration of a nutraceutical are contemplated for use in accordance with the present invention. While the illustrative examples described below use tablets as the solid matrix, alternative carrier media including but not limited to particles, granules, and the like may be used instead. Desirably, the particle size of such alternative carrier media is between about 10 and about 5000 microns, more desirably between about 50 and about 2000 microns. Moreover, a solid matrix in accordance with the present invention, which contains a polyphenol and a nutraceutical in an interior region, may optionally be coated with an outer layer that contains a bolus dose of nutraceutical in combination with methylcellulose, thereby enabling the rapid release of a first dose of nutraceutical upon consumption.

The specific amounts of one or more nutraceuticals in the solid matrix may vary with subject, type of malady to be treated, format of dosage form, etc. For example, the weight, age, and overall health of a subject may be factors in determining what constitutes a therapeutically effective amount for the particular subject. Similarly, the physical properties of a dosage form (e.g., increased surface areas of granules and particles as compared to tablets.) may be additional factors in determining a therapeutically effective amount. The therapeutically effective amount of nutraceutical is desirably selected to provide optimum efficacy for a particular application.

The following examples and comparative studies illustrate features in accordance with the present invention, and are provided solely by way of illustration. They are not intended to limit the scope of the appended claims or their equivalents.

EXAMPLES

The following materials were used in this study (product names and/or identifying characteristics and suppliers are included in parentheses): green tea extract, (Catepure 75% P.E., Xian Tiancheng Drug and Bioengineering Co., Tian Shanxi, China), riboflavin, USP-FCC (Roche Vitamins Inc., Parsippany, N.J.), silicified microcrystalline cellulose (Pro-Solv SMCC™ 90, Penwest Pharmaceuticals Co., Patterson, N.Y.), maltodextrin (Maltrin® M510, Grain Processing Corporation, Muscatine, Iowa), croscarmellose sodium, USP-NF (Nymcel ZSX, Noviant Inc., Morrow, Ga.), silicon dioxide, NF (Syloid® 244FP, Grace Division, Baltimore, Md.), magnesium stearate, vegetable 7205 (Mallinckrodt Inc, St. Louis, Mo.), dextrose (Undidex 020450, Corn Products Co., Marshall, Minn.), methylcellulose (Opadry® YS-2-7035, Colorcon, West Point, Pa.), hydroxypropyl methylcellulose (Methocel E5-LV, Dow Chemical Co., Midland, Mich.), glycerin (Optim Glycerine 99.7% USOP Kosher, Dow Chemical Co., Midland, Mich.).

The tablets prepared in these examples were compressed on a B2 press (J.J. Stokes Machine Co., Philadelphia, Pa.), using a Metropolitan Tablet Press Monitor (Metropolitan Computing Corporation, W. Orange, N.J.).

The spectrophotometric data was collected using a Beckman DU640 U-VIS spectrophotometer (Beckman Coulter, Inc., Fullerton, Calif.).

Example 1

Preparation of Coatings

A solution of hydroxypropyl methylcellulose was prepared by pumping 40 gallons of purified water into a jacketed 50 gallon stainless steel steam kettle. The water was heated to 55° C. Hydroxypropyl methylcellulose powder (17.0 kg) was slowly added to the water while being mixed with a Lightnin mixer (Rochester, N.Y.) at 500 rpm. Glycerin (1.703 kg) was added next. The solution was mixed for 4 to 6 minutes until all of the powder was fully dissolved. The solution was mixed for an additional 45 minutes at 300 rpm. The solution was cooled to room temperature and the foam was allowed to settle for at least 5 hours prior to using.

A solution of methylcellulose was prepared by pumping 41.3 gallons of purified water into a stainless steel tank. Methylcellulose/glycerin powder (11.048 kg, Opadry YS-2-7035) was slowly added to the water while it was being mixed with a Lightnin mixer at 600 rpm. The solution was mixed for an additional 60 minutes at 300 rpm.

Example 2

Preparation of Green Tea

Green tea and its extracts are commercially available in a variety of forms that may be used in accordance with the present invention. In the examples below, green tea originally in the form of a powder is instatized (i.e., agglomerated) in a fluid bed dryer prior to use. The instatized green tea (abbreviated "Green Tea Inst." in Tables 1–3, 6 and 8 below) is a convenient form for tablet preparation. However, it is to be understood that instatization of the green tea (or indeed of whatever polyphenol and/or nutraceutical is used in accordance with the present invention) is not required and that alternative forms may be employed.

Green tea extract (160 kg) was placed in a fluid bed dryer (Model T71110, Niro Inc, Aeromatic-Fielder AG, Bubendorf, Switzerland) and pre-fluidized for one minute. Water at 150° F. to 170° F. was then sprayed for 35 minutes at 1.2 kg/min and at an atomizer air pressure of 3.75 bar. The inlet air was set at 160° F. at an 11% flow rate. After achieving a rewet of approximately 24%, the material was dried, maintaining the inlet air temperature at 160° F. until moisture content fell to 3.0% or below.

Example 3

Effect of Methylcellulose on Sustained Release

A methylcellulose-coated tablet containing riboflavin and green tea was prepared as described below using the amounts shown in Table 1 and then evaluated for sustained release of riboflavin.

TABLE 1

| Description | Lot Wt. (kg) | Percent |
|---|---|---|
| Green Tea Inst. | 0.100 | 10.0 |
| Riboflavin | 0.100 | 10.0 |
| Prosolv | 0.345 | 34.4 |
| Maltodextrin 510 | 0.420 | 41.9 |
| Croscarmellose Sodium | 0.030 | 3.0 |
| Silicon Dioxide | 0.003 | 0.3 |
| Magnesium Stearate | 0.005 | 0.6 |

The tablet weight was 500 mg and 2006 tablets were compressed. Tablet shape and dimensions corresponded to 7/16" SC. The tablet weight was increased from 500 mg to 550 mg with the addition of dextrose to improve powder flow. Tablets were compressed at about 15 scu (Strong Cobb Units) hardness on a 16-station B2 instrumental press (J. J. Stokes Machine Co., Philadelphia, Pa.) with 7/16" standard cup tooling. 500 g of tablets were coated on a small O'Hara Labcoat 1 pan (O'Hara Technologies Inc., Toronto, Canada). The tablets were coated with methylcellulose up to a 1% weight gain. The samples (20 tablets) were pulled at 0%, 0.25%, 0.5%, 0.75%, and 1.0% at a spray rate of 6 mL/min, a pan speed of 18 rpm, an air flow of 220 cfm, and an inlet temperature of 60° C.

Three coated and three uncoated tablets were used for dissolution testing with USP Apparatus II. Samples (5-mL) were taken from each of the dissolution baths (Vankel VK 7000 Dissolution Tester, Vankel, Cary, N.C.) with coated tablets and filtered together into a flask. Samples (5-mL) were taken from each of the dissolution baths with uncoated tablets and filtered together into a flask. The baths were replenished with dilute HCl to maintain a constant volume throughout testing. Samples were taken over an 8-hour period.

Figure 2:
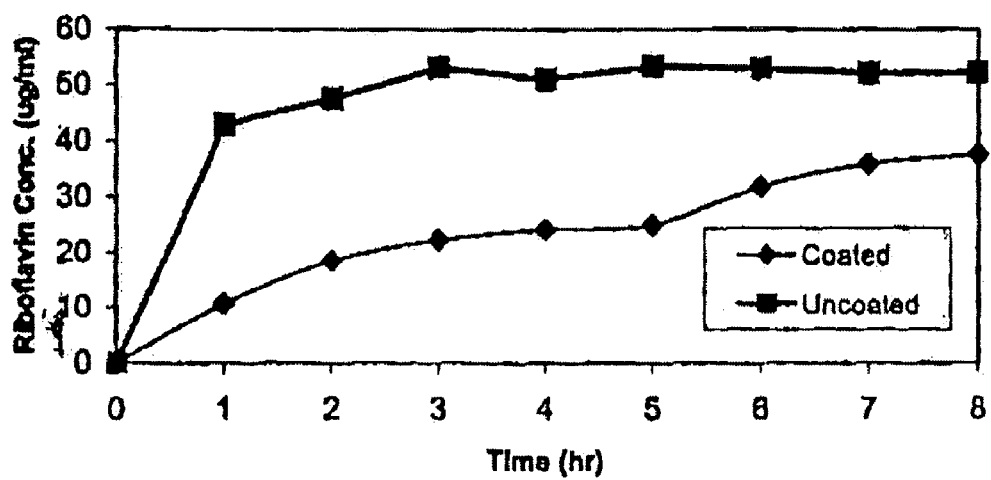
FIG. 2 shows a plot of riboflavin concentration versus time for an uncoated tablet and a tablet coated with methylcellulose.

The riboflavin content of the samples was tested using a spectrophotometric method. FIG. 1 shows the calibration curve generated, which plots absorbance at 444 nm versus riboflavin concentration. Samples were tested and the absorbance levels at 444 nm were recorded. As shown in the plot in FIG. 2, samples coated with methylcellulose exhibited substantially slower riboflavin release than the corresponding uncoated samples. For example, the uncoated tablet exhibits an approximately full release of riboflavin from the tablet after about 2–3 hours. In contrast, the methylcellulose-coated tablet does not show full release of riboflavin even after 8 hours, which is highly indicative of sustained release activity. As noted above, it is presently thought that the polyphenol (in this instance, a naturally-occurring green tea extract that contains polyphenols) interacts with methylcellulose to form a poorly soluble coating layer on the tablet which is responsible for the sustained release activity that is observed.

Figure 3:
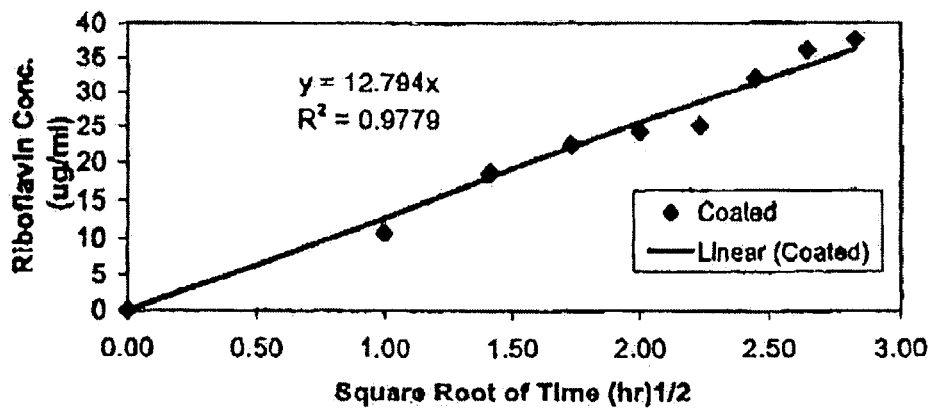
FIG. 3 shows a linear plot of riboflavin concentration versus square root of time, which corresponds to the dissolution of riboflavin from a methylcellulose-coated tablet.

FIG. 3 shows a plot of the dissolution of riboflavin indicating a linear relationship of riboflavin concentration with the square root of time. The linearity of the relationship between the quantity of nutraceutical released versus the square root of time is indicative of diffusion through the coating layer pores. This mechanism is described by the equation $Q=kt^{1/2}$, where Q represents the cumulative amount of nutraceutical released per surface area and t represents time. Such a mechanism typically applies to systems involving a water insoluble, permeable film. However, in the present case, the film appears to be permeable to both water and the active contents of the solid matrix.

Example 4

Effect of Green Tea on Sustained Release

Methylcellulose-coated tablets containing riboflavin and three different levels of green tea—0%, 5%, and 10% (w/w)—were prepared according to Tables 2–4 below. The tablets were then evaluated for sustained release of riboflavin.

TABLE 2

Riboflavin with 10% Green Tea

| Description | Lot Wt. (kg) | Percent |
|---|---|---|
| Green Tea Inst. | 0.100 | 10.0 |
| Riboflavin | 0.050 | 5.0 |
| Prosolv | 0.245 | 24.4 |
| Maltodextrin 510 | 0.570 | 66.8 |
| Croscarmellose Sodium | 0.030 | 3.0 |
| Silicon Dioxide | 0.003 | 0.3 |
| Magnesium Stearate | 0.005 | 0.6 |

TABLE 3

Riboflavin with 5% Green Tea

| Description | Lot Wt. (kg) | Percent |
|---|---|---|
| Green Tea Inst. | 0.050 | 5.0 |
| Riboflavin | 0.050 | 5.0 |
| Prosolv | 0.245 | 24.4 |
| Maltodextrin 510 | 0.620 | 61.8 |
| Croscarmellose Sodium | 0.030 | 3.0 |
| Silicon Dioxide | 0.003 | 0.3 |
| Magnesium Stearate | 0.005 | 0.5 |

TABLE 4

Riboflavin with 0% Green Tea

| Description | Lot Wt. (kg) | Percent |
|---|---|---|
| Riboflavin | 0.050 | 5.0 |
| Prosolv | 0.245 | 24.4 |
| Maltodextrin 510 | 0.670 | 66.8 |
| Croscarmellose Sodium | 0.030 | 3.0 |
| Silicon Dioxide | 0.003 | 0.3 |
| Magnesium Stearate | 0.005 | 0.5 |

Tablet ingredients were screened through a 20 mesh screen (W. S. Tyler, Inc., Mentor, Ohio) and bag-blended. Tablets were compressed on a 16-station B2 instrumental press equipped with a 7/16 inch round standard cup tooling. The applied compression force was 10–15 kN. Flowdex powder flow measurements were taken of the final blend prior to compression of the tablets. Tablets (500 g) were coated with methylcellulose to a 1% weight gain on an O'Hara Labcoat 1 (O'Hara Technologies Inc., Toronto, Canada) at 6 mL/minute at a pan speed of 18 rpm with a $T_{in}$ of 60° C. and air flow=220 cfm (cubic feet per minute).

Ten tablets were tested using an Erweka TBH 20 Tablet Tester (Heusenstamm, Germany). Dissolution tests were performed in triplicate using the Vankel VK 7000 Dissolution Tester (Vankel, Cary, N.C.) with USP Apparatus II. Tests were conducted with 900 mL of 0.1 N HCl (pH 1.0) at 37.0° C. and 75 rpm paddle speed. UV-VIS spectrophotometric measurements were conducted at 444 nm. The results of the tablet testing and flow results are summarized in Table 5 and FIG. 4 below.

TABLE 5

| | Weight (mg) | Hardness (scu) | Flowdex (mm) |
|---|---|---|---|
| 10% Green Tea | 503 | 15.8 | 24 |
| 5% Green Tea | 500 | 15.1 | 22 |
| 0% Green Tea | 498 | 14.7 | 22 |

Figure 4:
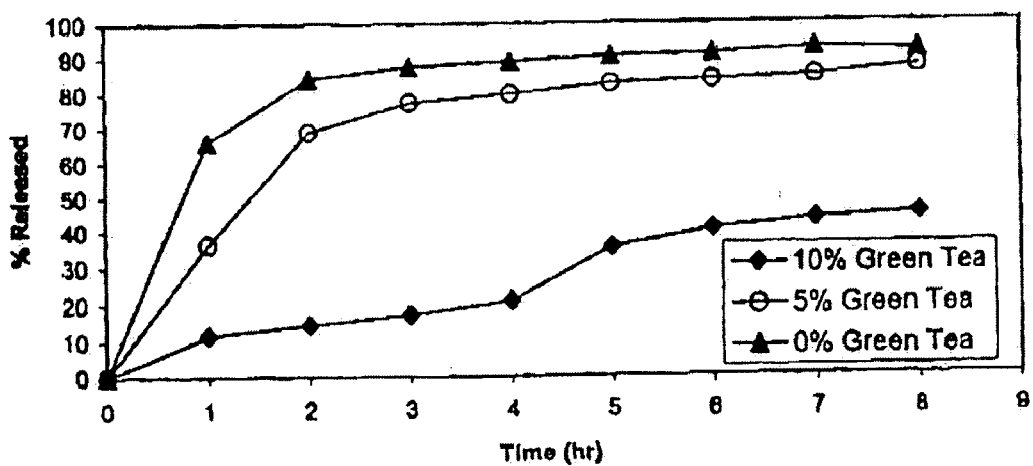
FIG. 4 shows a plot of the percent of riboflavin released versus time for methylcellulose-coated tablets containing 0%, 5%, and 10% green tea extract that includes polyphenols.

As shown in FIG. 4, essentially no sustained release occurs in the absence of green tea, whereas in the presence of 10% green tea, sustained release is evident. This experiment demonstrates that a polyphenol—in this instance green tea—used in accordance with the present invention is a contributing factor to sustained release activity.

Example 5

Comparing Effects of Methylcellulose and Hydroxypropyl Methylcellulose Coatings on Sustained Release A first batch of tablets containing 20% green tea and riboflavin were prepared as described below using the amounts shown in Table 6.

TABLE 6

Riboflavin with 20% Green Tea (First Batch)

| Description | Lot Wt. (kg) | Percent |
|---|---|---|
| Green Tea Inst. | 0.400 | 20.0 |
| Riboflavin | 0.100 | 5.0 |
| Prosolv | 0.600 | 30.0 |
| Maltodextrin 510 | 0.824 | 41.2 |
| Croscarmellose Sodium | 0.060 | 3.0 |
| Silicon Dioxide | 0.006 | 0.3 |
| Magnesium Stearate | 0.010 | 0.5 |

The characteristics of the first batch of tablets are shown in Table 7.

TABLE 7

Riboflavin with 20% Green Tea (First Batch)

| No. | Weight (mg) | Hardness (scu) |
|---|---|---|
| 1 | 501.7 | 16.9 |
| 2 | 498.4 | 14.8 |
| 3 | 496.3 | 14.5 |
| 4 | 501.8 | 16.5 |
| 5 | 503.2 | 15.5 |
| 6 | 501.3 | 16.9 |
| 7 | 501.9 | 15.5 |
| 8 | 501.1 | 16.4 |
| 9 | 497.4 | 14.5 |
| 10 | 502.1 | 15.9 |
| AVG | 500.52 | 15.74 |
| SD | 2.30 | 0.93 |

The tablet weight of the first batch was 500 mg and 4000 tablets were compressed. Tablet shape and dimensions corresponded to 7/16° SC. The tablets were compressed at about 15 scu hardness on a B2 press. The tablets (500 g) were coated up to a 5% weight gain on a small O'Hara pan with (1) methylcellulose (item no. NF9782) or (2) a 10/90 mixture by solids weight of hydroxypropyl methylcellulose to methylcellulose. Samples (20 tablets) coated with methylcellulose were pulled at 0%, 1.0%, 2.0%, 3.0%, 4.0%, and 5.0% at a spray rate of 6 mL/min, a speed of 18 rpm, and a temperature 60° C. The 10/90 mixture of hydroxypropyl methylcellulose to methylcellulose was made by blending 26.9 g of hydroxypropyl methylcellulose with 400 g of methylcellulose. Samples (20 tablets) coated with a 10/90 mixture of hydroxypropyl methylcellulose to methylcellulose were pulled at 0%, 1.0%, 2.0%, 3.0%, 4.0%, and 5.0% at a spray rate of 6 mL/min, a pan speed of 18 rpm, an air flow of 220 cfm, and an inlet temperature of 60° C.

A second batch of tablets containing 20% green tea and riboflavin were prepared as described below using the amounts shown in Table 8.

TABLE 8

Riboflavin with 20% Green Tea (Second Batch)

| Description | Lot Wt. (kg) | Percent |
|---|---|---|
| Green Tea Inst. | 0.400 | 20.0 |
| Riboflavin | 0.100 | 5.0 |
| Prosolv | 0.600 | 30.0 |
| Maltodextrin 510 | 0.824 | 41.2 |
| Croscarmellose Sodium | 0.060 | 3.0 |
| Silicon Dioxide | 0.006 | 0.3 |
| Magnesium Stearate | 0.010 | 0.5 |

The characteristics of the second batch of tablets are shown in Table 9.

TABLE 9

Riboflavin with 20% Green Tea (Second Batch)

| No. | Weight (mg) | Hardness (scu) |
|---|---|---|
| 1 | 492.8 | 12.9 |
| 2 | 503.3 | 15.2 |
| 3 | 491 | 13.2 |
| 4 | 501.5 | 14.7 |
| 5 | 501.5 | 14.1 |
| 6 | 495.6 | 14.3 |
| 7 | 495.3 | 13.8 |
| 8 | 502 | 15.3 |
| 9 | 503.3 | 15.5 |
| 10 | 501.1 | 14.8 |
| AVG | 498.74 | 14.38 |
| SD | 4.59 | 0.89 |

The tablet weight of the second batch was 500 mg and 4000 tablets were compressed. Tablet shape and dimensions corresponded to 7/16° SC. Tablets were compressed at about 15 scu hardness on a B2 press. The tablets (500 g) were coated up to a 5% weight gain on a small O'Hara pan with (1) hydroxypropyl methylcellulose or (2) a 30/70 mixture by solids weight of hydroxypropyl methylcellulose to methylcellulose. The 30/70 mixture of hydroxypropyl methylcellulose to methylcellulose was made by blending 82.6 g of hydroxypropyl methylcellulose with 318 g of methylcellulose. Samples (20 tablets) coated with a 30/70 mixture of hydroxpropyl methylcellulose to methylcellulose were pulled at 0%, 1.0%, 2.0%, 3.0%, 4.0%, and 5.0% at a spray rate of 6 mL/min, a pan speed of 18 rpm, an air flow of 220 cfm, and an inlet temperature of 60° C. Samples (20 tablets) coated with hydroxypropyl methylcellulose were pulled at 0%, 1.0% 2.0%, 3.0%, 4.0% and 5.0% at a spray rate of 6 mL/min, a pan speed of 18 rpm, an air flow of 220 cfm, and an inlet temperature of 60° C.; 227 g of hydroxypropyl methylcellulose was applied for a 5% weight gain.

Figure 5:
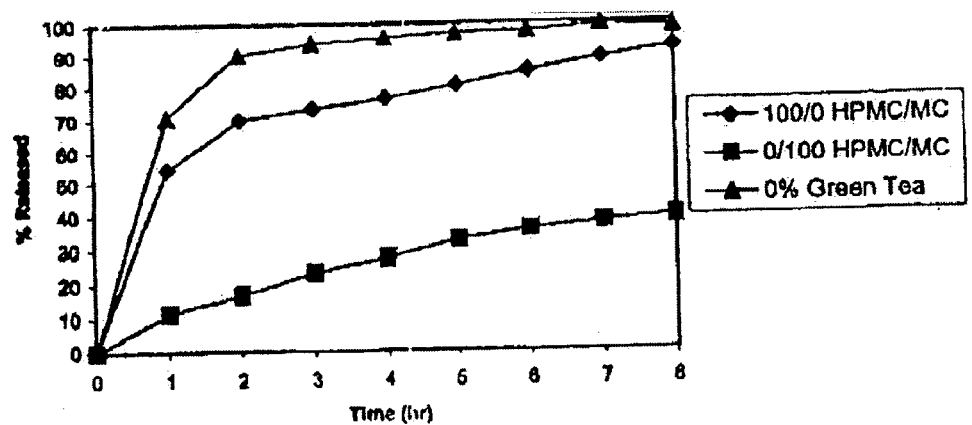
FIG. 5 shows a plot of the percent of riboflavin released versus time for first and second batches of tablets containing 20% green tea that includes polyphenols and coated to a 1% weight gain with either 100% hydroxypropyl methylcellulose or 100% methylcellulose, and for tablets coated with methylcellulose that contain no green tea.

FIG. 5 shows a plot of the percent riboflavin released versus time for (1) a tablet containing 20% green tea coated to a 1% weight gain with 100% hydroxypropyl methylcellulose, (2) a tablet containing 20% green tea coated to a 1% weight gain with 100% methylcellulose, and (3) a tablet coated with methylcellulose that contains no green tea. As shown by this plot, the tablet coated with 100% methylcellulose exhibits substantially slower sustained release than the tablet coated with 100% hydroxypropyl methylcellulose. For example, after 2 hours, the tablet coated with 100% hydroxypropyl methylcellulose has released about 70% of the riboflavin. In contrast, the tablet coated with 100% methylcellulose has released only about 15% of the riboflavin over this same time frame. Thus, after 2 hours, the tablet coated with 100% hydroxypropyl methylcellulose has released approximately five times more riboflavin than the tablet coated with 100% methylcellulose. Such a dramatic difference in sustained release characteristics is surprising and unexpected. As a point of reference, the tablet that contains no green tea has released about 90% of the riboflavin after only 2 hours.

Figure 6:
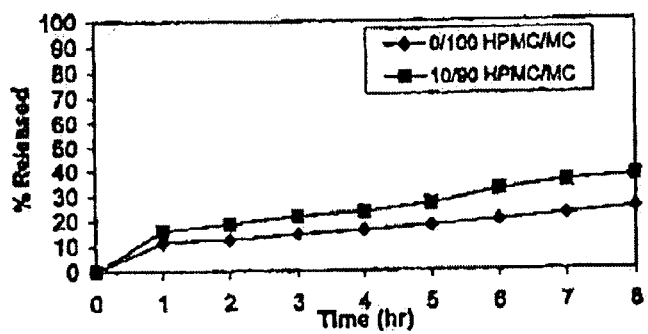
FIG. 6 shows a plot of the percent of riboflavin released versus time for a first batch of tablets containing 20% green tea that includes polyphenols and coated to a 5% weight gain with either 100% methylcellulose or a 10/90 mixture of hydroxypropyl methylcellulose to methylcellulose.

FIG. 6 shows a plot of the percent riboflavin released versus time for (1) a tablet containing 20% green tea coated to a 5% weight gain with 100% methylcellulose and (2) a tablet containing 20% green tea coated to a 5% weight gain with a 10/90 mixture of hydroxypropyl methylcellulose to methylcellulose. As shown by this plot, the tablet coated with 100% methylcellulose shows better sustained release than the tablet coated with the 10/90 mixture of hydroxypropyl methylcellulose to methylcellulose although the difference is smaller than those evident in FIG. 5. A comparison of FIGS. 5 and 6 shows that the tablet coated to a 5% weight gain with 100% methylcellulose (FIG. 6) exhibits slower sustained release characteristics than the tablet coated to a 1% weight gain with 100% methylcellulose (FIG. 5), a difference presumably due to the thicker coating in the case of the former. For example, after 8 hours, the tablet coated to a 1% weight gain with 100% methylcellulose has released about 38% of the riboflavin, whereas the tablet coated to a 5% weight gain with 100% methylcellulose has released only about 28% of the riboflavin.

Figure 7:
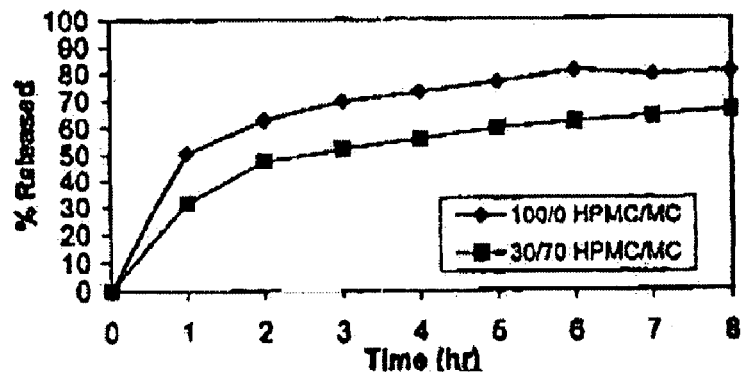
FIG. 7 shows a plot of the percent of riboflavin released versus time for a second batch of tablets containing 20% green tea that includes polyphenols and coated to a 5% weight gain with either 100% hydroxypropyl methylcellulose or a 30/70 mixture of hydroxypropyl methylcellulose to methylcellulose.

FIG. 7 shows a plot of the percent of riboflavin released versus time for the second batch of tablets containing 20% green tea and coated to a 5% weight gain with either (1) 100% hydroxypropyl methylcellulose or (2) a 30/70 mixture of hydroxypropyl methylcellulose to methylcellulose. As shown by this plot, tablets coated with the 30/70 mixture of hydroxypropyl methylcellulose to methylcellulose exhibit slower sustained release characteristics than tablets coated with 100% hydroxypropyl methylcellulose, a further indication of the surprisingly and unexpectedly advantageous effect of the presence of methylcellulose—even when admixed with hydroxypropyl methylcellulose—on sustained release characteristics. For example, after 8 hours, the tablet coated to a 5% weight gain with 100% hydroxypropyl methylcellulose has released about 78% of the riboflavin, whereas the tablet coated to a 5% weight gain with the 30/70 mixture of hydroxypropyl methylcellulose to methylcellulose has released only about 64% of the riboflavin.

Figure 8:
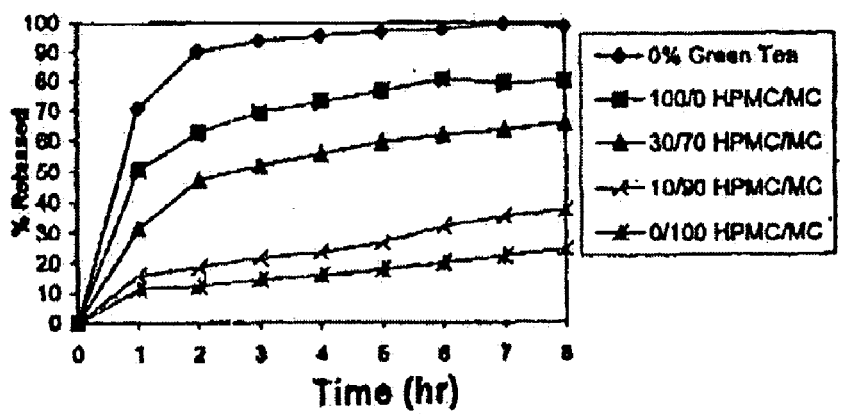
FIG. 8 shows a plot of the percent of riboflavin released versus time for tablets coated with methylcellulose that contain 0% green tea, tablets containing 20% green tea that includes polyphenols coated to a 5% weight gain with 100% hydroxypropyl methylcellulose, tablets containing 20% green tea that includes polyphenols coated to a 5% weight gain with a 30/70 mixture of hydroxypropyl methylcellulose to methylcellulose, tablets containing 20% green tea that includes polyphenols coated to a 5% weight gain with a 10/90 mixture of hydroxypropyl methylcellulose to methylcellulose, and tablets coated to a 5% weight gain with 100% methylcellulose.

FIG. 8 shows a plot of the percent of riboflavin released versus time for (1) tablets (Table 4) coated with methylcellulose that contain 0% green tea, (2) tablets (second batch) containing 20% green tea coated to a 5% weight gain with 100% hydroxypropyl methylcellulose, (3) tablets (second batch) containing 20% green tea coated to a 5% weight gain with a 30/70 mixture of hydroxypropyl methylcellulose to methylcellulose, (4) tablets (first batch) containing 20% green tea coated to a 5% weight gain with a 10/90 mixture of hydroxypropyl methylcellulose to methylcellulose, and (5) tablets (first batch) coated to a 5% weight gain with 100% methylcellulose. As shown by this plot, the slowest sustained release activity is exhibited by tablets coated with 100% methylcellulose, whereas the most rapid sustained release activity—apart from the tablets that contain no green tea—is exhibited by tablets coated with 100% hydroxypropyl methylcellulose. Tablets coated with mixtures of hydroxypropyl methylcellulose and methylcellulose exhibit intermediate levels of sustained release activity, as evident from the plot. The difference in sustained release activities between the two limiting extremes—that is, 100% hydroxypropyl methylcellulose and 100% methylcellulose—is dramatic, surprising, and unexpected.

Example 6

Effect of Coating Thickness on Sustained Release Activity

Figure 9:
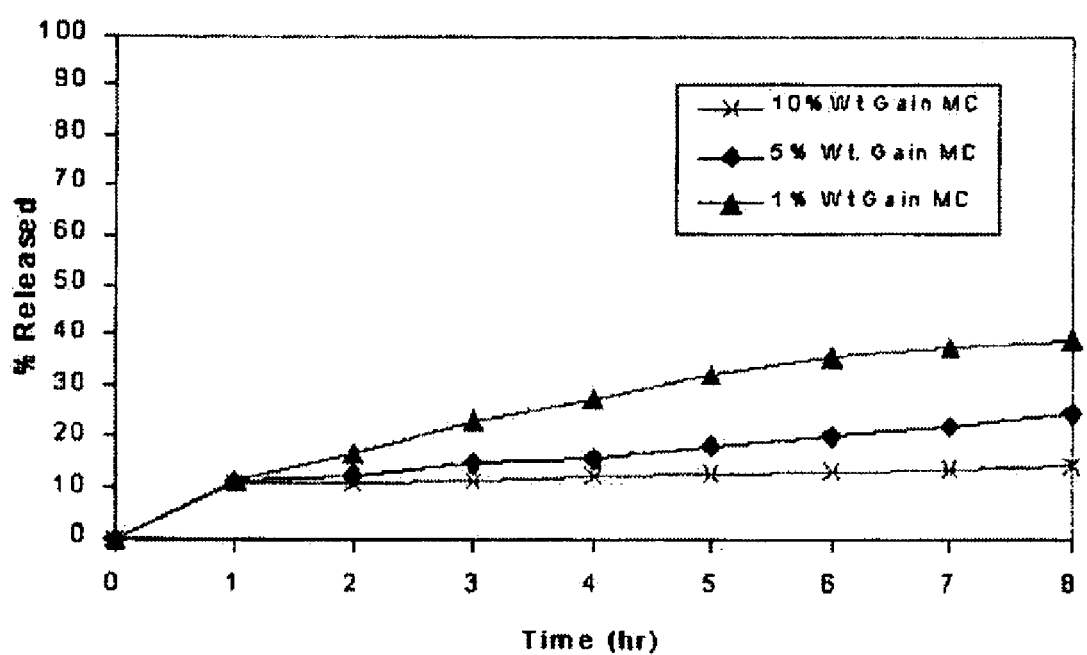
FIG. 9 shows a plot of the percent of riboflavin released versus time for tablets containing 20% green tea that includes polyphenols coated to a 1%, 5%, and 10% weight gain with methylcellulose.

FIG. 9 shows a plot of the percent of riboflavin released versus time for tablets from the above-described first batch containing 20% green tea and coated to a 1% and 5% weight gain with methylcellulose, and tablets from the above-described second batch containing 20% green tea and coated to a 10% weight with methylcellulose. As shown by this plot, the duration of sustained release increases with coating thickness. For example, after 8 hours, the tablets coated to a 10% weight gain have released only about 15% of the riboflavin, whereas the tablets coated to a 1% weight gain have released about 40% of the riboflavin.

Although the foregoing illustrative examples involve the use of green tea as the polyphenol, the present invention is by no means limited to such. All manner of polyphenols have been contemplated for use in accordance with the present invention including but not limited to the ones described hereinabove. Likewise, although the foregoing illustrative examples involve the use of riboflavin as the nutraceutical, the present invention is by no means limited to such. All manner of nutraceuticals have been contemplated for use in accordance with the present invention including but not limited to the ones described hereinabove.

Throughout this description and in the appended claims, it is to be understood that elements referred to in the singular (e.g., a polyphenol, a nutraceutical, and the like), refer to one or a plurality of such elements, regardless of the tense employed. Thus, for example, it is to be understood in the appended claims that a solid matrix embodying features of the present invention includes at least one polyphenol and a therapeutically effective amount of at least one nutraceutical.

The foregoing detailed description and examples have been provided by way of explanation and illustration, and are not intended to limit the scope of the appended claims. Many variations in the presently desirable embodiments illustrated herein will be obvious to one of ordinary skill in the art, and remain within the scope of the appended claims and their equivalents.

The invention claimed is:

1. A preparation for sustained release comprising a tablet coated with a coating comprising methylcellulose, wherein the tablet comprises about 10% green tea and riboflavin.

2. The preparation of claim 1 wherein the methylcellulose comprises at least about 80 percent by weight of the coating.

3. The preparation of claim 1 wherein the methylcellulose comprises at least about 90 percent by weight of the coating.

4. The preparation of claim 1 wherein the methylcellulose comprises about 100 percent by weight of the coating.

5. The preparation of claim 1 wherein the tablet further comprises an additional polyphenol which is selected from the group consisting of flavanols, flavonols, anthocyanins, flavonoids, cinnamate derivatives, and combinations thereof.

6. The preparation of claim 1 wherein the tablet further comprises an additional nutraceutical which is selected from the group consisting of antioxidants, antibiotics, antihistamines, antifungals, antimicrobials, analgesics, free radical scavengers, anti-tumor drugs, antiviral agents, HIV inhibitors, anti-inflammatory agents, antihepatoxic agents, anthelmintics, enzyme-inhibitors, vitamins, minerals, and combinations thereof.

7. The preparation of claim 6 wherein full release of the nutraceutical occurs over a time span of at least 3 hours.

8. The preparation of claim 6 wherein full release of the nutraceutical occurs over a time span of at least 5 hours.

9. The preparation of claim 6 wherein full release of the nutraceutical occurs over a time span of at least 8 hours.

10. The preparation of claim 6 wherein about 80% release of the nutraceutical occurs over a time span of at least 8 hours.

11. A preparation for sustained release comprising a tablet coated with a coating comprising at least about 90 percent by weight of methylcellulose, wherein the tablet comprises about 10% green tea, riboflavin and a therapeutically effective amount of an additional nutraceutical.

12. A method of controlled release of a preparation comprising administering to a patient the preparation of claim 1.

13. The preparation of claim 5, wherein the polyphenol comprises from about 1 to about 50 percent by weight of the tablet.

14. The preparation of claim 5, wherein the polyphenol comprises from about 3 to about 40 percent by weight of the tablet.

15. The preparation of claim 5, wherein the polyphenol comprises from about 5 to about 20 percent by weight of the tablet.

* * * * *